(12) United States Patent
Pasloske et al.

(10) Patent No.: US 12,303,519 B2
(45) Date of Patent: *May 20, 2025

(54) INJECTABLE PHARMACEUTICAL COMPOSITIONS COMPRISING A CYCLODEXTRIN A HYDROPHOBIC DRUG, A CO-SOLVENT, AND A PRESERVATIVE

(71) Applicant: Zoetis Services LLC, Parsippany, NJ (US)

(72) Inventors: Kirby Shawn Pasloske, New South Wales (AU); Kai Lau, New South Wales (AU); Sarah Jane Richardson, New South Wales (AU); Amanda Aileen Willis, New South Wales (AU)

(73) Assignee: Zoetis Services LLC, Parsippany, NJ (US)

( * ) Notice: Subject to any disclaimer, the term of this patent is extended or adjusted under 35 U.S.C. 154(b) by 536 days.

This patent is subject to a terminal disclaimer.

(21) Appl. No.: 16/224,433

(22) Filed: Dec. 18, 2018

(65) Prior Publication Data

US 2019/0125762 A1 May 2, 2019

Related U.S. Application Data

(63) Continuation of application No. 15/280,826, filed on Sep. 29, 2016, now Pat. No. 10,188,664, which is a
(Continued)

(30) Foreign Application Priority Data

Nov. 29, 2011 (AU) .................................. 2011904970
Nov. 9, 2012 (AU) .................................. 2012904962

(51) Int. Cl.
*A61K 47/69* (2017.01)
*A61K 9/00* (2006.01)
(Continued)

(52) U.S. Cl.
CPC .......... *A61K 31/573* (2013.01); *A61K 9/0019* (2013.01); *A61K 31/05* (2013.01);
(Continued)

(58) Field of Classification Search
CPC .. A61K 31/05; A61K 31/403; A61K 31/5415; A61K 31/57; A61K 9/0019;
(Continued)

(56) References Cited

U.S. PATENT DOCUMENTS

| | | | |
|---|---|---|---|
| 4,728,509 | A | 3/1988 | Shimizu et al. |
| 5,419,898 | A | 5/1995 | Ikejiri et al. |

(Continued)

FOREIGN PATENT DOCUMENTS

| | | |
|---|---|---|
| CA | 2597956 A1 | 8/2006 |
| CN | 101360503 A | 2/2009 |

(Continued)

OTHER PUBLICATIONS

CDC; "Questions about Multi-dose vials"; https://www.cdc.gov/injectionsafety/providers/provider_faqs_multivials.html; Feb. 9, 2011; Internet Archive record captured May 9, 2011; https://web.archive.org/web/20110509052819/https://www.cdc.gov/injectionsafety/providers/provider_faqs_multivials.html (Year: 2011).*

(Continued)

Primary Examiner — Timothy P Thomas
(74) Attorney, Agent, or Firm — Paul M. Misiak

(57) ABSTRACT

Injectable pharmaceutical compositions, methods of use and formulation are disclosed. The compositions comprise: one or more water soluble complexes, each complex comprising a cyclodextrin or a cyclodextrin derivative and a hydrophobic drug; at least one preservative; and at least one co-solvent. The compositions are effectively preserved in accordance with the European Pharmacopoeia 2011 Test for Efficacy of Antimicrobial Preservation, satisfying at least the (Continued)

B criteria as it applies to parenterals, and the United States Pharmacopeia 2011 Guidelines for Antimicrobial Effectiveness Testing, satisfying the criteria for Category 1 (injectable) products.

12 Claims, 2 Drawing Sheets

Related U.S. Application Data continuation of application No. 14/361,677, filed as application No. PCT/AU2012/001452 on Nov. 27, 2012, now Pat. No. 9,492,552.

(51) Int. Cl.

| | | |
|---|---|---|
| A61K 31/05 | (2006.01) | |
| A61K 31/14 | (2006.01) | |
| A61K 31/403 | (2006.01) | |
| A61K 31/5415 | (2006.01) | |
| A61K 31/57 | (2006.01) | |
| A61K 31/573 | (2006.01) | |
| A61K 45/06 | (2006.01) | |
| A61K 47/02 | (2006.01) | |
| A61K 47/10 | (2017.01) | |
| A61K 47/40 | (2006.01) | |
| A61P 23/00 | (2006.01) | |
| A61P 25/04 | (2006.01) | |
| A61P 29/00 | (2006.01) | |
| A61P 43/00 | (2006.01) | |
| B82Y 5/00 | (2011.01) | |
| C08B 37/16 | (2006.01) | |
| C08L 5/16 | (2006.01) | |

(52) U.S. Cl.
CPC ............ *A61K 31/14* (2013.01); *A61K 31/403* (2013.01); *A61K 31/5415* (2013.01); *A61K 31/57* (2013.01); *A61K 45/06* (2013.01); *A61K 47/02* (2013.01); *A61K 47/10* (2013.01); *A61K 47/40* (2013.01); *A61K 47/6951* (2017.08); *A61P 23/00* (2018.01); *A61P 25/04* (2018.01); *A61P 29/00* (2018.01); *A61P 43/00* (2018.01); *B82Y 5/00* (2013.01); *C08B 37/0015* (2013.01); *C08L 5/16* (2013.01)

(58) Field of Classification Search
CPC .... A61K 47/10; A61K 47/6951; A61K 47/40; A61P 23/00
See application file for complete search history.

(56) References Cited

U.S. PATENT DOCUMENTS

| | | |
|---|---|---|
| 6,358,935 B1 | 3/2002 | Beck et al. |
| 6,723,353 B2 | 4/2004 | Beck et al. |
| 6,969,706 B1 | 11/2005 | Chang et al. |
| 7,897,586 B2 | 3/2011 | Kieran et al. |
| 9,427,443 B2 | 8/2016 | Kieran et al. |
| 2003/0073665 A1 | 4/2003 | Thompson et al. |
| 2005/0239746 A1 | 10/2005 | Penkler et al. |
| 2007/0155697 A1 | 7/2007 | Adami et al. |
| 2012/0065186 A1 | 3/2012 | Li et al. |
| 2012/0316146 A1 * | 12/2012 | Goodchild ............ A61K 31/57 514/179 |

FOREIGN PATENT DOCUMENTS

| | | |
|---|---|---|
| EP | 0 605 203 A2 | 7/1994 |
| JP | S62123116 A | 6/1987 |
| JP | H06/239748 A | 8/1994 |
| JP | H06-293638 A | 10/1994 |
| JP | H09-048737 A | 2/1997 |
| JP | H11-512445 A | 10/1999 |
| JP | 2003-089632 A | 3/2003 |
| JP | 2004-182688 A | 7/2004 |
| JP | 2007-519703 A | 7/2007 |
| JP | 2011116776 | 6/2011 |
| WO | WO 96/32135 | 10/1996 |
| WO | WO 97/10805 | 3/1997 |
| WO | WO 01/70234 A1 | 9/2001 |
| WO | WO 01/97796 A1 | 12/2001 |
| WO | WO-2005082416 A2 * | 9/2005 ......... A61K 47/6951 |
| WO | WO2007/062339 A2 | 5/2007 |

OTHER PUBLICATIONS

Akers; "Chapter 41: Parenteral Preparations"; in Remington: The Science and Practice of Pharmacy; 21st Edition; Beringer et al. Eds.; 2005; Chapter 41 (Year: 2005).*

Australian Patent Application 2012268889; Filing date Nov. 27, 2012; Jurox Pty. Ltd.; Patent Examination Report No. 1 date of issue Jul. 26, 2013.

Australian Patent Application 201268889; filing date Nov. 27, 2012; Jurox Pty. Ltd.; patent Examination Report No. 2.

Bennett, "ViCAS Autumn 2011: Anaesthesia In Practice"; Sep. 2011; http://www.lovemypet.ie/wp-content/uploads/2012/02/RBennett_Surgery_module_1_notes.pdf.

Gould et al., 2-Hydroxypropyl-β-cycldextrin (HP-β-CD): A toxicology review, Food and Chemical Toxicology, 2005, pp. 1451-1459, vol. 43, Elsevier Ltd.

Lehner et al., Effect of Hydroxypropyl-β-cyclodextrin on the Antimicrobial Action of Preservatives, Journal of Pharmacy and Pharmacology, 1994, pp. 186-191, vol. 46, Wiley-Blackwell.

Lehner et al., Interactions between p-hydroxybenzoic acid esters and hydroxypropyl-β-cyclodextrin and their antimicrobial effect against *Candida albicans*, International Journal of Pharmaceutics, 1993, pp. 201-208, vol. 93, Elsevier Science Publishers B.V.

Loftsson, et al. Interactions Between Preservatives and 2-Hydroxypropyl-β-Cyclodextrin, Drug Development and Industrial Pharmacy, 1992, pp. 1477-1484, vol. 18, No. 13, Informa plc.

Moser et al.; "Comparison of Compendial Antimicrobial Effectiveness Tests: A Review", AAPS Pharmscitech (2011); vol. 12, No. 1, pp. 222-226.

Tachon et al.; "Assessment of the Allergenic Potential of Althesin and Its Constituents." 1983; British Journal of Anaesthesia; The Macmillan Press Ltd; vol. 55, Issue 8; pp. 715-717.

Vu et al.; "The Essentials of United States Pharmacopeia Chapter <51> Antimicrobial Effectiveness Testing", Int. J. Pharm. Comp., (2014); vol. 18, No. 2; pp. 123-130.

* cited by examiner

INJECTABLE PHARMACEUTICAL COMPOSITIONS COMPRISING A CYCLODEXTRIN A HYDROPHOBIC DRUG, A CO-SOLVENT, AND A PRESERVATIVE

RELATED APPLICATIONS

This application is a continuation of U.S. patent application Ser. No. 15/280,826, filed Sep. 29, 2016, which is a continuation of U.S. patent application Ser. No. 14/361,677, filed on May 29, 2014, which is a national stage entry of PCT International Application No. PCT/AU2012/001452, filed Nov. 27, 2012, which claims the benefit of Australian Provisional Patent Application No. 2011904970 filed on Nov. 29, 2011 and Australian Provisional Patent Application No. 2012904962 filed on Nov. 9, 2012, the content of which are incorporated herein by reference.

TECHNICAL FIELD

The invention relates to injectable pharmaceutical compositions which are effectively preserved in accordance with the European Pharmacopoeia 2011 Test for Efficacy of Antimicrobial Preservation, satisfying at least the B criteria as it applies to parenterals, and the United States Pharmacopeia 2011 Guidelines for Antimicrobial Effectiveness Testing, satisfying the criteria for Category 1 (injectable) products. The compositions can be stored in appropriately sized containers which allow for either a single dose or multiple doses to be taken. In addition, the invention provides methods to manufacture and use the herein defined compositions.

BACKGROUND OF THE INVENTION

Cyclodextrins are cyclic oligosaccharides which possess a toroidal structure and harbor hydrophobic/lipophilic central cavities and hydrophilic outer surfaces. A number of different cyclodextrin structures exist in nature, the most prominent being α-cyclodextrin, β-cyclodextrin and γ-cyclodextrin, which consist of 6, 7 and 8 glucopyranose units, respectively.

Cyclodextrins are known to increase the solubility of pharmaceuticals or drugs which are inherently insoluble or show a poor solubility in water. The employment of cyclodextrins and their derivatives helps to stabilize the drugs via the reversible formation of water soluble complexes. The formation of these complexes can prohibit or reduce the occurrence of side reactions that may take place between the drug and other species present in a solution. The drug molecule resides, either wholly or partly, within the central cavity of the cyclodextrin, or cyclodextrin derivative, to yield an inclusion complex. Consequently, various cyclodextrins and their derivatives have been deemed safe for use as pharmaceutical excipients, for example in Alfaxan® (WO 01/70234). Alfaxan® is an intravenous injectable anesthetic comprising complexes of alfaxalone and 2-hydroxy-β-cyclodextrin (obtainable from Jurox Pty Ltd). Typically β-cyclodextrin and β-cyclodextrin derivatives are utilized in the manufacture of medicaments. This is due to a number of reasons which includes the size of the lipophilic cavity, commercial availability, coupled with the low cost of the molecules, amongst other favorable attributes.

One important derivative is 2-hydroxypropyl-β-cyclodextrin which has been shown to be more water soluble and more toxicologically benign when compared to α-, β- and γ-cyclodextrin. Furthermore, in various studies, this derivative was shown to be tolerated in a range of animal species including rats, mice and dogs (S. Gould et al., Food and Chemical Technology, 43, 1451-1459, 2005).

When cyclodextrins and their derivatives are used to solubilize material in aqueous media, competition can occur between the various species present in the solution to occupy the central cavities of the cyclodextrin molecules. This means one compound may be solubilized to a greater degree in relation to any other compounds which may be present. This is an important point to consider when solubilizing pharmaceutical compounds with cyclodextrins, as ideally it is the active ingredient, e.g. a drug molecule, which is incorporated into the cyclodextrin and not any of the other excipients which may be present within a composition. For example, preservative species may be introduced into a liquid pharmaceutical composition in order to kill any bacteria, yeast or mold that may be accidently introduced into the composition. These preservative species may displace the drug molecule from the hydrophobic cavity of the cyclodextrin or cyclodextrin derivative, wherein the drug is unable to remain solubilized in the liquid medium and precipitates from the solution. The displacement of the drug molecule may lead to the formation of particulate matter, which has safety implications when the pharmaceutical composition is delivered via an injection.

The displacement of the drug means that the active pharmaceutical compound, for example a hydrophobic drug, is not fully solubilized. This then leads to a decreased efficacy, wherein the drug cannot perform its required function and induce the intended pharmacological and physiological response. In addition, in order for the preservative(s) to be effective against bacteria, yeast and mold, it/they should preferably remain unbound in the solution and not complexed in cyclodextrin hosts. If the preservative(s) form(s) complexes with the cyclodextrins in solution, the pharmaceutical composition may not meet preservation standards or adhere to prescribed regulations for medicaments.

Loftsson et al. (Drug Development and Industrial Pharmacy, 18 (13), 1477-1484, 1992), undertook a number of investigations which focused on 2-hydroxypropyl-β-cyclodextrin and its interactions with a selection of preservatives, including chlorobutanol, methylparaben, and propylparaben, which are commonly used in multi-dose pharmaceutical products. The interactions were shown to be twofold. Firstly, the chlorobutanol, methylparaben, and propylparaben molecules were able to displace drug molecules from the cyclodextrin cavity which, in turn, hindered the effectiveness of the cyclodextrin in solubilizing the hydrophobic drug. Secondly, the antimicrobial activity of the preservatives chlorobutanol, methylparaben, and propylparaben were reduced or completely suppressed in the presence of the 2-hydroxypropyl-β-cyclodextrin due to the sequestration of the preservatives.

A number of patents have utilized cyclodextrins to increase the solubility of drugs in order to improve their delivery, albeit to a limited degree.

WO 2001/70234 discloses a pharmaceutical composition comprising a water soluble cyclodextrin or a cyclodextrin derivative and alfaxalone. The composition is stable and can be administered, in an anesthetically effective amount, to warm blooded animals, including birds and mammals, reptiles, fish and amphibians. Although the invention can be utilized as an effective anesthetic, the patent does not disclose, teach, nor suggest a composition comprising both a co-solvent and a preservative.

U.S. Pat. Nos. 6,358,935 and 6,723,353 disclose pharmaceutically acceptable compositions which include a liquid medium, a cyclodextrin component, chlorite present in an effective preserving amount and a pharmaceutically active component. The formulations do not include a co-solvent.

WO 2005/082416 discloses formulations which comprise β-cyclodextrin, a pharmaceutically acceptable preservative, wherein the pharmaceutically acceptable preservatives are limited to meta-cresol, phenol, thimerosal, or combinations thereof, and an active pharmaceutical ingredient that is a neurokinin receptor antagonist. The invention relies on the binding value of the active pharmaceutical ingredient with the β-cyclodextrins, to be greater than that of the preservative with the equivalent β-cyclodextrin molecule. An optimal balance between the cyclodextrin and antimicrobial preservative concentrations is required in order for the composition to adhere to the preservation standards and achieve acceptable injection-site-toleration. The patent does not disclose aqueous formulations which comprise at least one preservative and at least one co-solvent.

Any discussion of documents, acts, materials, devices, articles or the like which has been included in the present specification is not to be taken as an admission that any or all of these matters form part of the prior art base or were common general knowledge in the field relevant to the present invention as it existed before the priority date of each claim of this application.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

SUMMARY OF THE INVENTION

Although pharmaceutical compositions can be stored and sealed for an extended period in inert surroundings, e.g. under a blanket of nitrogen in a vial, as soon as a seal is broken and the composition is exposed to an external environment, microbes and other pathogens may be introduced which may make the composition unsuitable for further use as a medicament.

Pharmaceutical compositions can be stored under a sterile environment without preservatives being present, but upon the broaching of the container holding the composition, any accidental introduction of microorganisms can deem the contents inappropriate for further use. Therefore, it is important to effectively preserve the pharmaceutical contents, especially when the pharmaceuticals are stored in large volumes. If a container holding a large volume of an unpreserved pharmaceutical composition is broached, the lack of a preservative may mean the majority of the contents are wasted.

Preservatives can be introduced into a pharmaceutical solution to kill bacteria, yeast and mold. The bacteria, yeast, and mold can be introduced accidentally when multiple aliquots are withdrawn from a container which holds multiple doses of a medicament. Unfortunately, problems may arise when the added preservatives interact detrimentally with other components within the composition yielding a reduced or complete lack of efficacy in regards to the pharmaceutical component(s) and/or the composition displays a reduced preservation effect. This can be seen in pharmaceutical compositions which contain preservatives and cyclodextrins or cyclodextrin derivatives.

In seeking to provide injectable pharmaceutical compositions which comply with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing, satisfying the criteria for Category 1 (injectable) products, the present inventors have established a new technique which allows injectable compositions to be produced and used wherein a hydrophobic drug or hydrophobic drugs is/are solubilized in water by the formation of inclusion complexes with cyclodextrin or cyclodextrin derivative molecules, in the presence of at least one preservative and at least one co-solvent without a loss of drug efficacy or preservation effect.

The present invention is directed to the problems encountered when using preservatives in combination with cyclodextrins or cyclodextrin derivatives and hydrophobic drugs, namely the competition between the preservatives and the hydrophobic drugs to occupy the cyclodextrin, or cyclodextrin derivative, central cavity.

When more than one hydrophobic drug is present in a pharmaceutical composition of the invention, each hydrophobic drug is able to form a water soluble complex with a cyclodextrin or cyclodextrin derivative present in the composition, even in the presence of at least one preservative, when at least one co-solvent is added.

In one aspect, the invention provides an injectable pharmaceutical composition complying with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products comprising:
  water,
  one or more water soluble complexes, each comprising a cyclodextrin or a cyclodextrin derivative and a hydrophobic drug,
  at least one preservative,
  at least one co-solvent and
  optionally a buffer effective to provide a pH in the composition in a range of from about 4.0 to about 9.0.

Throughout this specification, the phrase "one or more water soluble complexes, each comprising a cyclodextrin or a cyclodextrin derivative and a hydrophobic drug" means that the pharmaceutical composition can comprise one, or more than one hydrophobic drug, wherein each hydrophobic drug is able to form a water soluble complex with a cyclodextrin or cyclodextrin derivative present in the composition. Therefore, the invention allows for the pharmaceutical composition to comprise one type of water soluble complex, when only one hydrophobic drug is included in a composition of the invention, or more than one type of water soluble complex, when more than one hydrophobic drug is included in a composition of the invention.

In a preferred embodiment the injectable pharmaceutical composition has a minimum broached vial antimicrobial effectiveness of 7 days and preferably a broached vial antimicrobial effectiveness of 28 days or more.

In one embodiment, one hydrophobic drug is present in the injectable pharmaceutical composition complying with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products, wherein the hydrophobic drug is able to form a water soluble complex with a cyclodextrin or cyclodextrin derivative present in the composition.

In one embodiment, more than one hydrophobic drug is present in the injectable pharmaceutical composition complying with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products, wherein each hydrophobic drug is able to form a water soluble complex with a cyclodextrin or cyclodextrin derivative present in the composition.

In one embodiment, the injectable pharmaceutical composition complying with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products comprises at least one hydrophobic drug, wherein each hydrophobic drug is able to form a water soluble complex with a cyclodextrin or cyclodextrin derivative present in the composition, and further comprises at least one hydrophilic drug.

The present invention yields an injectable pharmaceutical composition, wherein the composition, stored in an appropriate sealed container, remains viable for delivery via injection and with no detrimental effects seen with the hydrophobic drug or drugs for an extended period of at least 7 days, preferably 28 days or more, once the container is broached and the container is stored at room temperature.

The invention allows for the pharmaceutical compositions to be effectively preserved once a container is broached for a period of at least 7 days, preferably 28 days or more, when stored in an appropriate container, in volumes for either a single dose or for multiple doses. In addition, the pharmaceutical compositions can be stored at room temperature even after broaching and do not require a refrigerated environment, although the invention is not limited to preclude it.

The ability to store a pharmaceutical composition at room temperature is advantageous. Typically an individual, for example a veterinarian, administering an injectable composition that had been stored under cold temperatures would wait for the injectable composition to warm to room temperature prior to administering the drug in order to avoid possible discomfort to the patient upon injection and to allow for ease of injection, i.e. viscosity. The ability to store a broached vial at room temperature is much more convenient to this individual as it avoids the need to wait for the composition to warm up before it can be used.

The present invention is directed to the problem of a preservative displacing a hydrophobic drug from a water soluble complex comprised of a cyclodextrin or a cyclodextrin derivative and a hydrophobic drug by the introduction of at least one co-solvent into a pharmaceutical composition. The use of a co-solvent or co-solvents allows for at least one preservative to be present without any detrimental effects occurring with regards to both the hydrophobic drug present in the water soluble complex and the preservative, i.e. the pharmaceutical composition retains the desired therapeutic effect and the composition complies with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products.

The binding between the hydrophobic drug and the cyclodextrin or cyclodextrin derivative is reversible. Therefore, the invention provides a pharmaceutical composition that once delivered via injection allows the hydrophobic drug to be displaced from the cyclodextrin or cyclodextrin derivative molecule to deliver the desired treatment and/or induce the required pharmacological response and/or physiological result.

A 7 day limit is the minimum time period the composition must remain viable after broaching i.e. the pharmaceutical composition is effectively preserved, and the complexed hydrophobic drug, or complexed hydrophobic drugs when more than one hydrophobic drug is present, once delivered via injection, is/are able to induce the required pharmacological and physiological response(s). Preferably the time period is 28 days or more.

The present invention allows the injectable pharmaceutical compositions to be stored in an appropriately sized container which holds enough of the composition for a single dose of a medicament, wherein the composition is effectively preserved for a period of at least 7 days, preferably 28 days or more when the container is broached. In addition, the present invention also allows the injectable pharmaceutical compositions to be stored in an appropriately sized container which holds enough of the composition for multiple doses of a medicament, wherein the composition is effectively preserved for a period of at least 7 days, preferably 28 days or more when the container is broached. Multiple doses, or aliquots, of the composition can be taken from the container without any detrimental effect on the preservatives or the hydrophobic drug over a period of at least 7 days, preferably 28 days or more i.e. the composition is effectively preserved for at least 7 days, preferably 28 days or more.

In another aspect, the invention provides a method to produce an injectable pharmaceutical composition complying with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products, wherein the method comprises:

preparing a first composition by:
  a) dissolving a cyclodextrin or cyclodextrin derivative or a mixture thereof in water;
  b) adding one or more hydrophobic drugs to the solution;
  c) optionally introducing additional water to fully dissolve the cyclodextrin or cyclodextrin derivative and the one or more hydrophobic drugs;
  d) optionally adding buffer salts;
  e) optionally adjusting the pH;
preparing a second composition by:
  dissolving at least one preservative in one or more co-solvent(s);
and forming the injectable pharmaceutical composition by:
  a) combining the first and second compositions;
  b) optionally adding additional water to raise the combined composition to a required volume; and
  c) sterilizing the combined composition.

In a preferred embodiment, the method of producing an injectable pharmaceutical composition provides an injectable pharmaceutical composition having a minimum broached vial antimicrobial effectiveness of 7 days, preferably a broached vial antimicrobial effectiveness of 28 days or more.

In another embodiment, the method of producing a pharmaceutical composition further comprises at least one hydrophilic drug, wherein the at least one hydrophilic drug(s) is/are added in the making of the first composition, second composition, or the forming of the injectable pharmaceutical composition.

In one embodiment when preparing the first composition the pH is adjusted by the addition of an acidic aqueous solution. In another embodiment the acidic aqueous solution is hydrochloric acid.

In another embodiment, in the preparing of the first composition the pH is adjusted by the addition of a basic aqueous solution. In another embodiment the basic aqueous solution is sodium hydroxide.

In another embodiment, one or more additional preservatives are incorporated into the injectable pharmaceutical composition. Any additional preservatives may be added in the first composition along with the optional buffering salts.

In yet another embodiment, one or more additional co-solvents may be included in the injectable pharmaceutical composition. Any additional co-solvents may be added after the optional pH adjustment in the first composition and prior to the mixing of the first and second compositions to form the injectable pharmaceutical composition.

In one embodiment, the injectable pharmaceutical composition may be sterilized by moist heat sterilization, which includes sterilization autoclaving, or by aseptic sterilization via filtration, or by radiation sterilization.

In another aspect, the invention provides a method of preserving an injectable pharmaceutical composition comprising:
  water,
  one or more water soluble complexes, each comprising a cyclodextrin or a cyclodextrin derivative and a hydrophobic drug and
  optionally a buffer effective to provide a pH in the composition in a range of from about 4.0 to about 9.0
by including an effective amount of at least one preservative and at least one co-solvent in the composition.

In a preferred embodiment, the method of preserving an injectable pharmaceutical composition provides an injectable pharmaceutical composition having a minimum broached vial antimicrobial effectiveness of 7 days, preferably 28 days or more.

The effective amount of at least one preservative and at least one co-solvent in the injectable pharmaceutical composition means the concentration of the at least one preservative and the concentration of the at least one co-solvent is sufficient for the injectable pharmaceutical composition to have a minimum broached vial antimicrobial effectiveness of 7 days, preferably 28 days or more.

In another embodiment, the method of preserving an injectable pharmaceutical composition provides an injectable pharmaceutical composition that complies with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products.

In another embodiment for the method of preserving a pharmaceutical composition, the injectable pharmaceutical composition comprises one hydrophobic drug.

In another embodiment for the method of preserving a pharmaceutical composition, the injectable pharmaceutical composition comprises more than one hydrophobic drug.

In yet another embodiment for the method of preserving a pharmaceutical composition, the injectable pharmaceutical composition comprises at least one hydrophobic drug and further comprises at least one hydrophilic drug.

In another aspect, the invention provides a use of at least one co-solvent and at least one preservative to preserve an injectable pharmaceutical composition comprising:
  water,
  one or more water soluble complexes, each comprising a cyclodextrin or a cyclodextrin derivative and a hydrophobic drug and
  optionally a buffer effective to provide a pH in the composition in a range of from about 4.0 to about 9.0,
by introducing at least one co-solvent and at least one preservative into the composition.

In a preferred embodiment, the use of at least one co-solvent and at least one preservative to preserve an injectable pharmaceutical composition provides an injectable pharmaceutical composition having a minimum broached vial antimicrobial effectiveness of 7 days, preferably a broached vial antimicrobial effectiveness of 28 days or more.

In another embodiment, the use of at least one co-solvent and at least one preservative to preserve an injectable pharmaceutical composition provides an injectable pharmaceutical composition that complies with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products.

In another embodiment, the invention provides a use of at least one co-solvent and at least one preservative to preserve an injectable pharmaceutical composition as herein described wherein the injectable pharmaceutical composition comprises one hydrophobic drug.

In another embodiment, the invention provides a use of at least one co-solvent and at least one preservative to preserve an injectable pharmaceutical composition as herein described wherein the injectable pharmaceutical composition comprises more than one hydrophobic drug.

In another embodiment, the invention provides a use of at least one co-solvent and at least one preservative to preserve an injectable pharmaceutical composition as herein described wherein the injectable pharmaceutical composition comprises at least one hydrophobic drug and further comprises at least one hydrophilic drug.

In another aspect, the invention provides an injectable pharmaceutical composition of the invention for treating an animal. In one embodiment the treatment is for at least one of the purposes of: anaesthetizing the animal, alleviating pain, or alleviating inflammation.

Herein the term "animal" comprises: warm blooded animals, including mammals (comprising but not limited to dogs, cats, cattle, pigs sheep, and horses), reptiles, fish, and amphibians.

In another aspect, the invention provides an injectable pharmaceutical composition of the invention for treating a human being. In one embodiment the treatment is for the purpose of anaesthetizing the human being.

In another aspect, the invention provides a method of treating an animal, comprising administering to an animal an injectable pharmaceutical composition of the invention. In one embodiment the treatment is for at least one of the purposes of: anaesthetizing the animal, alleviating pain, or alleviating inflammation.

In another aspect, the invention provides a method of treating a human being, comprising administering to a human being an injectable pharmaceutical composition of the invention. In one embodiment the treatment is for the purpose of anaesthetizing the human being.

In another aspect, the invention provides a use of an injectable pharmaceutical composition of the invention, in the preparation of a medicament for treating an animal. In one embodiment the treatment is for at least one of the purposes of: anaesthetizing the animal, alleviating pain, or alleviating inflammation.

The invention also provides a use of an injectable pharmaceutical composition of the invention, in the preparation of a medicament for treating a human being. In one embodiment the treatment is for the purpose of anaesthetizing the human being.

Figure 1:
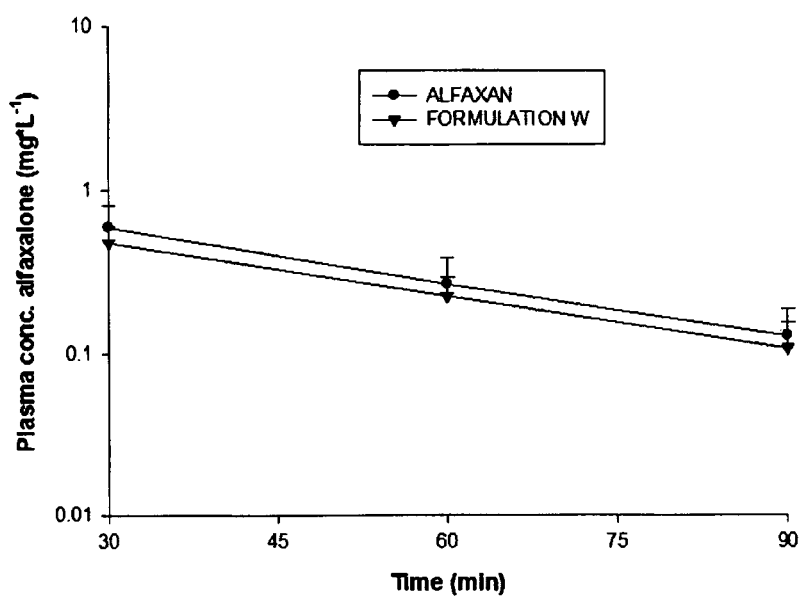
FIG. 1—Discloses the concentration of alfaxalone in plasma (mg/L) versus time after IV administration of Alfaxan® or Formulation W (Table 1) to dogs (n=12 per time point).

Alfaxan® is an intravenous injectable anesthetic comprising complexes of alfaxalone and 2-hydroxy-β-cyclodextrin (obtainable from Jurox Pty Ltd).

DETAILED DESCRIPTION OF THE INVENTION

Buffer

In a preferred embodiment the invention optionally comprises a buffer effective to stabilize the hydrophobic drug or drugs in the injectable pharmaceutical composition, and provides a pH in a range of from about 4.0 to about 9.0.

In another embodiment, the buffer, if present, can be chosen from the group comprising: phosphate based, acid-phosphate based and citrate based buffers.

In another embodiment the buffer, if present, is phosphate based.

In another embodiment the buffer, if present, is acid-phosphate based.

In yet another embodiment the buffer, if present, is citrate based.

In yet another embodiment the buffer, if present, is a combination of phosphate and citrate based buffers.

Preservatives

In the current invention at least one preservative is present in the injectable pharmaceutical composition.

A number of preservatives are available which can kill or prevent the growth of commonly encountered contaminants; these contaminants include, but are not limited to: the bacteria *P. aeruginosa, E. coli* and *S. aureus*; the yeast *C. albicans*; and the mold *A. brasiliensis*.

The presence of at least one preservative allows for the injectable pharmaceutical composition to be used over a period of at least 7 days, preferably 28 days or more once the container holding the composition is broached. The injectable pharmaceutical composition has a minimum broached vial antimicrobial effectiveness of 7 days and preferably a broached vial antimicrobial effectiveness of 28 days or more. The minimum duration is 7 days, after broaching, for the preservative/preservatives present to be effective and may allow for the pharmaceutical composition to be viable for use and/or treatment beyond this period. Preferably this time period is 28 days or more.

The incorporation of a preservative or preservatives within the pharmaceutical composition does not hinder the solubility of the hydrophobic drug or drugs and the final compositions are still able to pass a test method complying with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products when the compositions are comprised of at least one co-solvent and one or more water soluble complexes, each complex comprised of a cyclodextrin, or a cyclodextrin derivative, and a hydrophobic drug. Nor does the presence of an optional buffer, effective to stabilize the hydrophobic drug or drugs and provide a pH in the composition in a range of from about 4.0 to about 9.0, hinder the preservative from passing the necessary preservative tests applied to the composition.

In a preferred embodiment at least one preservative is present in the pharmaceutical composition and can be selected from a group comprising but not limited to: m-cresol, chlorocresol, parabens including but not limited to methylparaben, ethylparaben, propylparaben, butylparaben, their derivatives, and salts, chlorobutanol, quaternary ammonium compounds, their derivatives, and salts including benzethonium chloride, benzalkonium chloride, boric acid, benzyl alcohol, cetylpyridinium chloride, cetrimide, phenol, phenylethanol, phenoxyethanol, and mixtures thereof.

The preservative or preservatives are present in an amount which is effective to impart the desired preservative characteristics and allows the final composition to comply with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products.

In one embodiment the injectable pharmaceutical composition comprises m-cresol, wherein the m-cresol is present in an amount in a range of about 0.1 to about 1% w/v, preferably in a range of about 0.1 to about 0.5% w/v, most preferably in a range of about 0.1 to about 0.2% w/v.

In one embodiment the injectable pharmaceutical composition comprises chlorocresol, wherein the chlorocresol is present in an amount in a range of about 0.1 to about 1% w/v, preferably in a range of about 0.1 to about 0.5% w/v, most preferably in a range of about 0.1 to about 0.2% w/v.

In one embodiment the injectable pharmaceutical composition comprises methyl-, ethyl-, propyl-, or butyl-paraben, wherein the methyl-, ethyl-, propyl-, or butyl-paraben is present in an amount in a range of about 0.005 to about 1% w/v, preferably in a range of about 0.01 to about 0.5% w/v, most preferably in a range of about 0.01 to about 0.2% w/v.

In another embodiment the injectable pharmaceutical composition comprises chlorobutanol, wherein the chlorobutanol is present in an amount in a range of about 0.05 to about 1% w/v, preferably in a range of about 0.05 to about 0.5% w/v, most preferably in a range of about 0.1 to about 0.5% w/v.

In another embodiment the injectable pharmaceutical composition comprises benzethonium chloride, wherein the benzethonium chloride is present in an amount in a range of about 0.005 to about 1% w/v, preferably in a range of about 0.005 to about 0.1% w/v, most preferably in a range of about 0.005 to about 0.05% w/v. In another embodiment the injectable pharmaceutical composition comprises benzalkonium chloride, wherein the benzalkonium chloride is present in an amount in a range of about 0.001 to about 1% w/v, preferably in a range of about 0.001 to about 0.5% w/v, most preferably in a range of about 0.001 to about 0.05% w/v.

In another embodiment the injectable pharmaceutical composition comprises boric acid, wherein the boric acid is present in an amount in a range of about 0.25 to about 5% w/v, preferably in a range of about 0.25 to about 2% w/v, most preferably in a range of about 0.25 to about 1% w/v.

In another embodiment the injectable pharmaceutical composition comprises benzyl alcohol, wherein the benzyl alcohol is present in an amount in a range of about 0.1 to about 5% w/v, preferably in a range of about 0.1 to about 2% w/v, most preferably in a range of about 0.1 to about 1% w/v.

In another embodiment the injectable pharmaceutical composition comprises cetylpyridinium chloride, wherein the cetylpyridinium chloride is present in an amount in a range of about 0.0001 to about 0.5% w/v, preferably in a range of about 0.0001 to about 0.01% w/v, most preferably in a range of about 0.0001 to about 0.001% w/v.

In another embodiment the injectable pharmaceutical composition comprises cetrimide, wherein the cetrimide is present in an amount in a range of about 0.001 to about 1.0% w/v, preferably in a range of about 0.001 to about 0.5% w/v, most preferably in a range of about 0.001 to about 0.01% w/v.

In another embodiment the injectable pharmaceutical composition comprises phenol, wherein the phenol is present in an amount in a range of about 0.05 to about 1% w/v, preferably in a range of about 0.05 to about 0.5% w/v, most preferably in a range of about 0.05 to about 0.1% w/v.

In another embodiment the injectable pharmaceutical composition comprises phenylethanol, wherein the phenylethanol is present in an amount in a range of about 0.1 to about 2% w/v, preferably in a range of about 0.1 to about 1.5% w/v, most preferably in a range of about 0.1 to about 1.0% w/v.

In another embodiment the injectable pharmaceutical composition comprises phenoxyethanol, wherein the phenoxyethanol is present in an amount in a range of about 0.1 to about 2% w/v, preferably in a range of about 0.1 to about 1.5% w/v, most preferably in a range of about 0.1 to about 1.0% w/v.

In yet another embodiment injectable pharmaceutical composition is comprised of a mixture of any of the recited preservatives disclosed herein, wherein each preservative is present in an amount stated in the ranges as disclosed herein.

Solvent

In the present invention the solvent is water. In a preferred embodiment the water is pharmaceutically quality purified water. In another preferred embodiment the pharmaceutical composition contains sufficient water to produce a composition of the invention in the desired dosage.

Co-Solvents

The current invention incorporates at least one co-solvent into the injectable pharmaceutical composition.

In a preferred embodiment the co-solvent or co-solvents are miscible with water.

The invention provides at least one co-solvent to be present in the injectable pharmaceutical composition, which allows a hydrophobic drug to remain in the hydrophobic cavity of a cyclodextrin or cyclodextrin derivative in the presence of at least one preservative.

When more than one hydrophobic drug is present in the injectable pharmaceutical composition, the presence of at least one co-solvent means that each hydrophobic drug is able to remain in the hydrophobic cavity of a cyclodextrin or cyclodextrin derivative in the presence of at least one preservative.

In a preferred embodiment the co-solvent or co-solvents can be selected from the group comprising, but not limited to: ethanol, glycerin, propylene glycol, isopropyl alcohol, glycerol formal, tetraglycol, polyethylene glycol, and mixtures thereof.

The co-solvent or co-solvents are present in the composition in a pharmaceutically acceptable amount that does not stop the preservative or preservatives which are also present from complying with a test method complying with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products.

In one embodiment the injectable pharmaceutical composition comprises ethanol, wherein the ethanol is present in an amount in a range of about 1 to about 30% w/v, preferably in a range of about 1 to about 25% w/v, most preferably in a range of about 1 to about 20% w/v.

In another embodiment the injectable pharmaceutical composition comprises glycerin, wherein the glycerin is present in an amount in a range of about 1 to about 30% w/v, preferably in a range of about 1 to about 25% w/v, most preferably in a range of about 1 to about 20% w/v.

In another embodiment the injectable pharmaceutical composition comprises propylene glycol, wherein the propylene glycol is present in an amount in a range of about 1 to about 30% w/v, preferably in a range of about 1 to about 25% w/v, most preferably in a range of about 1 to about 20% w/v.

In another embodiment the injectable pharmaceutical composition comprises isopropyl alcohol, wherein the isopropyl alcohol is present in an amount in a range of about 1 to about 30% w/v, preferably in a range of about 1 to about 25% w/v, most preferably in a range of about 1 to about 20% w/v.

In another embodiment the injectable pharmaceutical composition comprises glycerol formal, wherein the glycerol formal is present in an amount in a range of about 1 to about 30% w/v, preferably in a range of about 1 to about 25% w/v, most preferably in a range of about 1 to about 20% w/v.

In another embodiment the injectable pharmaceutical composition comprises tetraglycol, wherein the tetraglycol is present in an amount in a range of about 1 to about 30% w/v, preferably in a range of about 1 to about 25% w/v, most preferably in a range of about 1 to about 20% w/v.

In another embodiment the injectable pharmaceutical composition comprises polyethylene glycol, wherein the polyethylene glycol is present in an amount in a range of about 1 to about 30% w/v, preferably in a range of about 1 to about 25% w/v, most preferably in a range of about 1 to about 20% w/v In yet another embodiment the injectable pharmaceutical composition is comprised of a mixture of any of the recited co-solvents disclosed herein, wherein each co-solvent is present in an amount stated in the ranges above.

Cyclodextrin and Cyclodextrin Derivatives

The present invention provides an injectable pharmaceutical composition comprising one or more water soluble complexes, each complex comprising a cyclodextrin or a cyclodextrin derivative and a hydrophobic drug.

The cyclodextrin or cyclodextrin derivative is chosen in order to enhance the solubility of a hydrophobic drug in water by the formation of a water soluble complex.

The hydrophobic drug and cyclodextrin or cyclodextrin derivative form a host guest complex wherein the hydrophobic drug is the guest and the cyclodextrin or cyclodextrin derivative is the host.

The invention allows for one, or more than one, hydrophobic drug to be present in the pharmaceutical composition. Each hydrophobic drug is able to form a water soluble complex with a cyclodextrin or cyclodextrin derivative present in the pharmaceutical composition.

In a preferred embodiment the cyclodextrin or cyclodextrin derivative can be chosen from a group that is comprised of, but is not limited to: α-cyclodextrin, β-cyclodextrin, γ-cyclodextrin, methyl substituted cyclodextrins, ethyl substituted cyclodextrins, hydroxyalkyl substituted cyclodextrins, including 2-hydroxypropyl-β-cyclodextrin, alkyl ether cyclodextrins, branched cyclodextrins, cationic cyclodextrins, quaternary ammonium cyclodextrins, anionic cyclodextrins, amphoteric cyclodextrins, sulfoalkyl ether β-cyclodextrins, or a modified form thereof, and mixtures thereof.

The specific cyclodextrin or cyclodextrin derivative is chosen so as to form a water soluble complex with a hydrophobic drug that can be utilized in an injectable pharmaceutical composition complying with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products. The composition further comprises water, at least one co-solvent, at least one preservative and optionally a buffer effective to stabilize the hydrophobic drug, or drugs, and provide a pH in the composition in a range of from about 4.0 to about 9.0.

The cyclodextrin or cyclodextrin derivative is chosen so as to form water soluble complexes with a hydrophobic drug, or drugs when more than one hydrophobic drug is present, wherein the complexes are stable in water and wherein, once the pharmaceutical composition is delivered via injection, the hydrophobic drug is displaced from the cyclodextrin or cyclodextrin derivative molecule to deliver the desired pharmacological and physiological response.

In a preferred embodiment the binding of a hydrophobic drug to the cavity of a cyclodextrin or cyclodextrin derivative in a water soluble complex is reversible allowing the hydrophobic drug to be displaced from the cyclodextrin or cyclodextrin derivative upon the injection of the composition which incorporates the water soluble complexes.

The amount of cyclodextrin or cyclodextrin derivative present in the invention is sufficient to solubilize the hydrophobic drug, or drugs if more than one hydrophobic drug is present, selected so as to form stable water soluble complexes.

In one embodiment the cyclodextrin derivative is preferably 2-hydroxypropyl-β-cyclodextrin.

In one embodiment the injectable pharmaceutical composition comprises a cyclodextrin or cyclodextrin derivative, wherein the cyclodextrin or cyclodextrin derivative is present in an amount in a range of about 1 to about 50% w/v, preferably in a range of about 1 to about 40% w/v, most preferably in a range of about 5 to about 25% w/v.

In yet another preferred embodiment the injectable pharmaceutical composition comprises 2-hydroxypropyl-β-cyclodextrin, wherein the 2-hydroxypropyl-β-cyclodextrin derivative is present in an amount in a range of about 1 to about 50% w/v, preferably in a range of about 1 to about 40% w/v, most preferably in a range of about 5 to about 25% w/v.

Hydrophobic Drugs

The invention provides for a hydrophobic drug, or drugs, each contained within complexes, each complex comprising a cyclodextrin or a cyclodextrin derivative, to be preserved and solubilized for a period of at least 7 days, preferably 28 days or more, whereby the drug(s) remain(s) active and viable for the intended treatment in a patient for at least 7 days, preferably 28 days or more in the presence of at least one preservative and at least one co-solvent, once a vial has been broached.

The invention allows for one or more than one hydrophobic drug to be present in the pharmaceutical composition. Each hydrophobic drug is able to form a water soluble complex with a cyclodextrin or cyclodextrin derivative present in the pharmaceutical composition.

The invention may further comprise at least one hydrophilic drug.

In a preferred embodiment, the hydrophobic drug, or drugs, is/are selected in that it/they can be delivered via injection.

The hydrophobic drug, or drugs, is/are combined with an appropriately selected cyclodextrin or cyclodextrin derivative to form a water soluble complex which is included in a pharmaceutical composition which further comprises: water, at least one preservative, at least one co-solvent and optionally a buffer effective to stabilize the hydrophobic drug and provide a pH in the composition in a range of from about 4.0 to about 9.0, wherein the composition can be delivered via injection and wherein the pharmaceutical composition complies with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products.

The hydrophobic drug, or drugs, is/are preserved after broaching for at least 7 days, preferably 28 days or more in an injectable pharmaceutical composition and stored as a medicament in volumes appropriate for single or multiple doses.

The hydrophobic drug, or drugs, is/are combined with an appropriately selected cyclodextrin or cyclodextrin derivative to form a water soluble complex that once delivered via injection, the hydrophobic drug, or drugs is/are displaced from the central cavity of the cyclodextrin or cyclodextrin derivative and induce the required physiological and pharmacological response.

The hydrophobic drug, or drugs, is/are stable once it/they has/have been complexed with the appropriate cyclodextrin or cyclodextrin derivative to form water soluble complexes, in the presence of at least one co-solvent and at least one preservative wherein the co-solvent or co-solvents and preservative or preservatives are appropriately chosen, prior to being delivered by injection.

In one preferred embodiment the hydrophobic drug, or drugs, can be chosen from a group that is comprised of, but is not limited to:

Steroids, their derivatives and salts including alfaxalone (alphaxalone), prednisolone, hydrocortisone, alphadolone (alfadolone), allopregnanolone, alphadolone (alfadolone) acetate, and pro-drugs thereof Oxicam NSAIDs, their derivatives and salts including meloxicam, piroxicam, and pro-drugs thereof Propionic acids, their derivatives and salts including carprofen, ibuprofen, naproxen, and pro-drugs thereof Phenols, their derivatives and salts including propofol, and pro-drugs thereof Benzimidazoles, their derivatives and salts including albendazole, triclabendazole, and pro-drugs thereof Hexahydropyrazines, their derivatives and salts including praziquantel, and pro-drugs thereof Beta-lactams, their derivatives and salts including ampicillin, penicillin, cefixime, and pro-drugs thereof.

Sulfonamides, their derivatives and salts, and pro-drugs thereof

Pyridines and pyrimidines, their derivatives and salts, and pro-drugs thereof

Oxazolidones, their derivatives and salts, and pro-drugs thereof

Ansamycins, their derivatives and salts, and pro-drugs thereof

Glycopeptides, their derivatives and salts, and pro-drugs thereof

Benzodiazepines, their derivatives and salts including diazepam, and pro-drugs thereof Hormones, their derivatives and salts including estradiol, and pro-drugs thereof Amino-amides, their derivatives and salts including lidocaine, and pro-drugs thereof Barbiturates, their derivatives and salts including thiopental, and pro-drugs thereof Salicylates, their derivatives and salts including aspirin, and pro-drugs thereof Salicylanilides, their derivatives and salts including closantel, and pro-drugs thereof.

The hydrophobic drug, or drugs, is/are present in an amount sufficient to induce the required therapeutic effect(s) in a patient when delivered via injection.

In one embodiment, the hydrophobic drug, or drugs, is/are appropriately chosen by a person skilled in the art, to be effective when treating an animal from the group comprising: warm blooded animals, including birds and mammals, reptiles, fish, and amphibians.

In another embodiment, the hydrophobic drug, or drugs, is/are appropriately chosen by a person skilled in the art, to be effective when treating an animal from the group comprising: dogs, cats, cattle, pigs, sheep, and horses.

In one embodiment, the hydrophobic drug, or drugs, is/are appropriately chosen by a person skilled in the art, to be effective when treating a human being.

In one embodiment, the hydrophobic drug is an anesthetic.

In another embodiment, the hydrophobic drug is an anesthetic for animals including: warm blooded animals, including birds and mammals, reptiles, fish, and amphibians.

In another embodiment, the hydrophobic drug is an anesthetic for a human being.

In another embodiment, one hydrophobic drug is present in the injectable pharmaceutical composition, wherein the one hydrophobic drug is selected from alfaxalone, meloxicam, propofol, or carprofen.

In another embodiment, more than one hydrophobic drug is present in the injectable pharmaceutical composition, wherein at least one hydrophobic drug is selected from alfaxalone, meloxicam, propofol, or carprofen.

In yet another embodiment, the hydrophobic drug is alfaxalone, wherein the alfaxalone is present in an amount in a range of from about 1 to about 100 mg/mL, more preferably about 1 to about 75 mg/mL, most preferably about 1 to about 50 mg/mL.

In a further embodiment, the hydrophobic drug is propofol, wherein the propofol is present in an amount in a range of from about 1 to about 100 mg/mL, more preferably about 1 to about 75 mg/mL, most preferably about 1 to about 50 mg/mL.

In another embodiment, the hydrophobic drug is meloxicam, wherein the meloxicam is present in an amount in a range of from about 1 to about 100 mg/mL, more preferably about 1 to about 75 mg/mL, most preferably about 1 to about 50 mg/mL.

In yet another embodiment, the hydrophobic drug is carprofen, wherein the carprofen is present in an amount in a range of from about 1 to about 100 mg/mL, more preferably about 1 to about 75 mg/mL, most preferably about 1 to about 50 mg/mL.

In yet another embodiment, a composition of the invention can further comprise a compound which enhances the solubility of a hydrophobic drug or drugs as herein described. Examples of compounds which enhance the solubility of meloxicam in a composition of the invention can be selected from the group comprising, but not limited to N-vinylpyrrolidone polymers.

In another embodiment the N-vinylpyrrolidone polymers have a molecular formula of $(C_6H_9NO)_n$, where n is in a range from about 20 to about 27,000 providing polymers with molecular weights from about 2,220 g mol$^{-1}$ to about 3,108,000 g mol$^{-1}$.

In a further embodiment, the N-vinylpyrrolidone polymers, if present in a composition of the invention, are included in a concentration from about 1% w/v to about 20% w/v, preferably from about 1% w/v to about 10% w/v, most preferably from about 1% w/v to about 5% w/v.

In yet another embodiment a compound which enhances the solubility of a hydrophobic drug or drugs as herein described in a composition of the invention can also modify the viscosity of said composition.

Hydrophilic Drugs

The invention provides for the injectable pharmaceutical composition to optionally further comprise at least one hydrophilic drug.

In one embodiment the hydrophilic drug can be chosen from the group comprised of but not limited to: opioids, including but not limited to tramadol and its M1 metabolite, buprenorphine, opioid like substances and $\alpha_2$-adrenergic agonists including, but not limited to, medetomidine.

In one embodiment the injectable pharmaceutical composition comprises tramadol and its M1 metabolite, wherein the tramadol and its M1 metabolite is present in an amount in a range of about 1 to about 200 mg/mL, preferably in a range of about 10 to about 100 mg/mL, most preferably in a range of about 25 to about 75 mg/mL.

In one embodiment the injectable pharmaceutical composition comprises buprenorphine, wherein the buprenorphine is present in an amount in a range of about 0.01 to about 5 mg/mL, preferably in a range of about 0.1 to about 1 mg/mL, most preferably in a range of about 0.1 to about 0.5 mg/mL.

In one embodiment the injectable pharmaceutical composition comprises medetomidine, wherein the medetomidine is present in an amount in a range of about 0.01 to about 10 mg/mL, preferably in a range of about 0.05 to about 5 mg/mL, most preferably in a range of about 0.1 to about 2 mg/mL.

In one embodiment, the injectable pharmaceutical composition comprises one or more hydrophobic drug(s), as described herein, and further comprises at least one hydrophilic drug, wherein each of the one or more hydrophobic drug(s) forms a water soluble complex with an appropriately chosen cyclodextrin or cyclodextrin derivative. The at least one hydrophilic drug, as described herein, is present in an amount sufficient to induce the required pharmacological and physiological response.

In another embodiment, the injectable pharmaceutical composition comprises one or more hydrophobic drug(s), wherein at least one hydrophobic drug is selected from alfaxalone, meloxicam, propofol, or carprofen, and further comprises at least one hydrophilic drug, as described herein, wherein each of the one or more hydrophobic drug(s) forms a water soluble complex with an appropriately chosen cyclodextrin or cyclodextrin derivative. The at least one hydrophilic drug is present in an amount sufficient to induce the required pharmacological and physiological response.

In yet another embodiment, the injectable pharmaceutical composition allows for combination analgesic injections comprising oxicam NSAIDs and opioids and/or opioid like substances as described herein.

In one embodiment, the hydrophilic drug or drugs, is/are appropriately chosen by a person skilled in the art, to be effective when treating an animal from the group comprising: warm blooded animals, including birds and mammals, reptiles, fish, and amphibians In another embodiment, the hydrophilic drug, or drugs, is/are appropriately chosen by a person skilled in the art, to be effective when treating an animal from the group comprising: dogs, cats, cattle, pigs, sheep, and horses.

In yet another embodiment, the hydrophilic drug or drugs, is/are appropriately chosen by a person skilled in the art, to be effective when treating a human being.

Isotonic Agent

The injectable pharmaceutical compositions of the invention as disclosed herein can further comprise an isotonic agent. Examples of isotonic agents include, but are not limited to sodium chloride and dextrose.

In one embodiment the isotonic agent is sodium chloride or dextrose wherein the sodium chloride or dextrose is present in a composition of the invention in an amount which renders the composition isotonic with the blood of a subject being treated.

In another embodiment the isotonic agent is sodium chloride, wherein the sodium chloride is present in an amount of about 0.9% w/v.

In another embodiment the isotonic agent is dextrose, wherein the dextrose is present in an amount of about 5% w/v.

Stability

The stability of the injectable compositions is very important. In general terms the compositions described herein will be physically and chemically stable for at least 3 months when stored below 30° C., preferably at least 6 months when stored below 30° C., more preferably at least 1 year when stored below 30° C., most preferably at least 3 years when stored below 30° C.

EXAMPLES EMBODIMENTS

A. An injectable pharmaceutical composition complying with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products comprising:
water,
one or more water soluble complexes, each comprising a cyclodextrin or a cyclodextrin derivative and a hydrophobic drug,
at least one preservative,
at least one co-solvent and
optionally a buffer effective to provide a pH in the composition in a range of from about 4.0 to about 9.0.

B. The injectable pharmaceutical composition according to example embodiment A, wherein at least one hydrophobic drug is selected from a group comprising: alfaxalone, propofol, meloxicam, and carprofen.

C. The injectable pharmaceutical composition according to example embodiment B, wherein:
alfaxalone is present in an amount in a range of from about 1 to about 100 mg/mL, more preferably about 1 to about 75 mg/mL, most preferably about 1 to about 50 mg/mL; and/or
propofol is present in an amount in a range of from about 1 to about 100 mg/mL, more preferably about 1 to about 75 mg/mL, most preferably about 1 to about 50 mg/mL; and/or
meloxicam is present in an amount in a range of from about 1 to about 100 mg/mL, more preferably about 1 to about 75 mg/mL, most preferably about 1 to about 50 mg/mL; and/or
carprofen is present in an amount in a range of from about 1 to about 100 mg/mL, more preferably about 1 to about 75 mg/mL, most preferably about 1 to about 50 mg/mL.

D. The injectable pharmaceutical composition according to any one of example embodiments A to C, wherein the cyclodextrin or cyclodextrin derivative is selected from a group comprising: α-cyclodextrin, β-cyclodextrin, γ-cyclodextrin, methyl substituted cyclodextrins, ethyl substituted cyclodextrins, hydroxyalkyl substituted cyclodextrins, including 2-hydroxypropyl-β-cyclodextrin, alkyl ether cyclodextrins, branched cyclodextrins, cationic cyclodextrins, quaternary ammonium cyclodextrins, anionic cyclodextrins, amphoteric cyclodextrins, sulfoalkyl ether β-cyclodextrins, or a modified form thereof, and mixtures thereof E. The injectable pharmaceutical composition according to any one of example embodiments A to D, wherein the cyclodextrin or cyclodextrin derivative is 2-hydroxypropyl-β-cyclodextrin.

F. The injectable pharmaceutical composition according to any one of example embodiments A to E, wherein at least one preservative is selected from a group comprising: m-cresol, chlorocresol, parabens (including, but not limited to: methylparaben, ethylparaben, propylparaben, or butylparaben), their derivatives and salts, chlorobutanol, benzethonium chloride, benzalkonium chloride, boric acid, benzyl alcohol, cetylpyridinium chloride, cetrimide, phenol, phenylethanol, phenoxyethanol, and mixtures thereof.

G. The injectable pharmaceutical composition according to any one of example embodiments A to F, wherein at least one co-solvent is selected from a group comprising: ethanol, glycerin, propylene glycol, isopropyl alcohol, glycerol formal, tetraglycol, and mixtures thereof H. The injectable pharmaceutical composition according to any one of example embodiments A to G, wherein the buffer effective to stabilize the hydrophobic drug and provide a pH in the composition in a range of from about 4.0 to about 9.0 is selected from a group of buffers comprising: phosphate based, acid-phosphate based, and citrate based buffers.

I. The injectable pharmaceutical composition according to any one of example embodiments A to H, wherein the composition further comprises at least one hydrophilic drug.

J. A method to produce an injectable pharmaceutical composition complying with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products, wherein the method comprises:
preparing a first composition by:
  a) dissolving a cyclodextrin or cyclodextrin derivative or a mixture thereof in water;
  b) adding one or more hydrophobic drugs to the solution;
  c) optionally introducing additional water to fully dissolve the cyclodextrin or cyclodextrin derivative and the one or more hydrophobic drugs;
  d) optionally adding buffer salts;
  e) optionally adjusting the pH;
preparing a second composition by:
  dissolving at least one preservative in one or more co-solvent(s);
and forming the injectable pharmaceutical composition by:
  a) combining the first and second compositions;
  b) optionally adding additional water to raise the combined composition to a required volume; and
  c) sterilizing the combined composition.

K. The method according to example embodiment J, wherein the cyclodextrin or cyclodextrin derivative is selected from a group comprising: α-cyclodextrin, β-cyclodextrin, γ-cyclodextrin, methyl substituted cyclodextrins, ethyl substituted cyclodextrins, hydroxyalkyl substituted cyclodextrins, including 2-hydroxypropyl-β-cyclodextrin, alkyl ether cyclodextrins, branched cyclodextrins, cationic cyclodextrins, quaternary ammonium cyclodextrins, anionic cyclodextrins, amphoteric cyclodextrins, sulfoalkyl ether β-cyclodextrins or a modified form thereof, and mixtures thereof L. The method according to example embodiment J or K, wherein at least one hydrophobic drug is selected from a group comprising: alfaxalone, propofol, meloxicam, and carprofen.

M. The method according to any one of example embodiments J to L, wherein:
alfaxalone is present in an amount in a range of from about 1 to about 100 mg/mL, more preferably about 1 to about 75 mg/mL, most preferably about 1 to about 50 mg/mL; and/or
propofol is present in an amount in a range of from about 1 to about 100 mg/mL, more preferably about 1 to about 75 mg/mL, most preferably about 1 to about 50 mg/mL; and/or
meloxicam is present in an amount in a range of from about 1 to about 100 mg/mL, more preferably about 1 to about 75 mg/mL, most preferably about 1 to about 50 mg/mL; and/or
carprofen is present in an amount in a range of from about 1 to about 100 mg/mL, more preferably about 1 to about 75 mg/mL, most preferably about 1 to about 50 mg/mL.

N. The method according to any one of example embodiments J to M, wherein at least one preservative is selected from a group comprising: m-cresol, chlorocresol, parabens including but not limited to methylparaben, ethylparaben, propylparaben, butylparaben, their derivatives and salts, chlorobutanol, quaternary ammonium compounds, their derivatives and salts including benzethonium chloride and benzalkonium chloride, boric acid, benzyl alcohol, cetylpyridinium chloride, cetrimide, phenol, phenylethanol, phenoxyethanol and mixtures thereof O. The method according to any one of example embodiments J to N, wherein the one or more co-solvent(s) are selected from a group comprising: ethanol, glycerin, propylene glycol, isopropyl alcohol, glycerol formal, tetraglycol, and mixtures thereof.

P. The method according to any one of example embodiments J to 0, wherein the buffer is effective to stabilize the hydrophobic drug and provide a pH in the first composition in a range of from about 4.0 to about 9.0 and is selected from a group of buffers comprising: phosphate based, acid-phosphate based, and citrate based buffers.

Q. The method according to any one of example embodiments J to P, wherein the injectable pharmaceutical composition is sterilized by autoclaving.

R. The method according to any one of example embodiments J to Q, wherein the pharmaceutical composition further comprises at least one hydrophilic drug, wherein the at least one hydrophilic drug is added in the making of the first, second, or the forming of the injectable pharmaceutical composition.

S. A method of preserving an injectable pharmaceutical composition comprising:
water,
one or more water soluble complexes, each comprising a cyclodextrin or a cyclodextrin derivative and a hydrophobic drug and
optionally a buffer effective to provide a pH in the composition in a range of from about 4.0 to about 9.0
by including an effective amount of at least one preservative and at least one co-solvent in the composition.

T. The method according to example embodiment S, wherein the cyclodextrin or cyclodextrin derivative is selected from a group comprising: α-cyclodextrin, β-cyclodextrin, γ-cyclodextrin, methyl substituted cyclodextrins, ethyl substituted cyclodextrins, hydroxyalkyl substituted cyclodextrins, including 2-hydroxypropyl-β-cyclodextrin, alkyl ether cyclodextrins, branched cyclodextrins, cationic cyclodextrins, quaternary ammonium cyclodextrins, anionic cyclodextrins, amphoteric cyclodextrins, sulfoalkyl ether β-cyclodextrin, or a modified form thereof, and mixtures thereof.

U. The method according to example embodiment S or T, wherein at least one hydrophobic drug is selected from a group comprising: alfaxalone, propofol, meloxicam, and carprofen.

V. The method according to any one of example embodiments S to U, wherein:
alfaxalone is present in an amount in a range of from about 1 to about 100 mg/mL, more preferably about 1 to about 75 mg/mL, most preferably about 1 to about 50 mg/mL; and/or
propofol is present in an amount in a range of from about 1 to about 100 mg/mL, more preferably about 1 to about 75 mg/mL, most preferably about 1 to about 50 mg/mL; and/or
meloxicam is present in an amount in a range of from about 1 to about 100 mg/mL, more preferably about 1 to about 75 mg/mL, most preferably about 1 to about 50 mg/mL; and/or
carprofen is present in an amount in a range of from about 1 to about 100 mg/mL, more preferably about 1 to about 75 mg/mL, most preferably about 1 to about 50 mg/mL.

W. The method according to any one of example embodiments S to V, wherein at least one preservative is selected from a group comprising: m-cresol, chlorocresol, parabens (including but not limited to methylparaben, ethylparaben, propylparaben or butylparaben), their derivatives and salts, chlorobutanol, quaternary ammonium compounds, their derivatives and salts including benzethonium chloride and benzalkonium chloride, boric acid, benzyl alcohol, cetylpyridinium chloride, cetrimide, phenol, phenylethanol, phenoxyethanol, and mixtures thereof.

X. The method according to any one of example embodiments S to W, wherein at least one co-solvent is selected from a group comprising: ethanol, glycerin, propylene glycol, isopropyl alcohol, glycerol formal, tetraglycol, and mixtures thereof.

Y. The method according to any one of example embodiments S to X, wherein the buffer is effective to stabilize the hydrophobic drug and provide a pH in the first composition in a range of from about 4.0 to about 9.0 and is selected from a group of buffers comprising: phosphate based, acid-phosphate based, and citrate based buffers.

Z. The method according to any one of example embodiments S to Y, wherein the injectable pharmaceutical composition complies with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products.

AA. The method according to any one of example embodiments S to Z, wherein the pharmaceutical composition further comprises at least one hydrophilic drug.

AB. Use of at least one co-solvent and at least one preservative to preserve an injectable pharmaceutical composition comprising:
water,
one or more water soluble complexes, each comprising a cyclodextrin or a cyclodextrin derivative and a hydrophobic drug and
optionally a buffer effective to provide a pH in the composition in a range of from about 4.0 to about 9.0,
by introducing at least one co-solvent and at least one preservative into the composition.

AC. The use according to example embodiment AB, wherein the cyclodextrin or cyclodextrin derivative is selected from a group comprising: α-cyclodextrin, β-cyclodextrin, γ-cyclodextrin, methyl substituted cyclodextrins, ethyl substituted cyclodextrins, hydroxyalkyl substituted cyclodextrins, including 2-hydroxypropyl-β-cyclodextrin, alkyl ether cyclodextrins, branched cyclodextrins, cationic cyclodextrins, quaternary ammonium cyclodextrins, anionic cyclodextrins, amphoteric cyclodextrins, sulfoalkyl ether β-cyclodextrins, or a modified form thereof, and mixtures thereof.

AD. The use according to example embodiment AB or AC, wherein at least one hydrophobic drug is selected from a group comprising: alfaxalone, propofol, meloxicam, and carprofen.

AE. The use according to any one of example embodiments AB to AD, wherein:
alfaxalone is present in an amount in a range of from about 1 to about 100 mg/mL, more preferably about 1 to about 75 mg/mL, most preferably about 1 to about 50 mg/mL; and/or
propofol is present in an amount in a range of from about 1 to about 100 mg/mL, more preferably about 1 to about 75 mg/mL, most preferably about 1 to about 50 mg/mL; and/or
meloxicam is present in an amount in a range of from about 1 to about 100 mg/mL, more preferably about 1 to about 75 mg/mL, most preferably about 1 to about 50 mg/mL; and/or
carprofen is present in an amount in a range of from about 1 to about 100 mg/mL, more preferably about 1 to about 75 mg/mL, most preferably about 1 to about 50 mg/mL.

AF. The use according to any one of example embodiments AB to AE, wherein at least one preservative is selected from a group comprising: m-cresol, chlorocresol, parabens (including but not limited to methylparaben, ethylparaben, propylparaben, or butylparaben), their derivatives and salts, chlorobutanol, quaternary ammonium compounds, their derivatives and salts including benzethonium chloride and benzalkonium chloride, boric acid, benzyl alcohol, cetylpyridinium chloride, cetrimide, phenol, phenylethanol, phenoxyethanol, and mixtures thereof.

AG. The use according to any one of example embodiments AB to AF, wherein at least one co-solvent is selected from a group comprising: ethanol, glycerin, propylene glycol, isopropyl alcohol, glycerol formal, tetraglycol, and mixtures thereof.

AH. The use according to any one of example embodiments AB to AG, wherein the buffer is effective to stabilize the hydrophobic drug and provide a pH in the first composition in a range of from about 4.0 to about 9.0 and is selected from a group of buffers comprising: phosphate based, acid-phosphate based, and citrate based buffers.

AI. The use according to any one of example embodiments AB to AH, wherein the injectable pharmaceutical composition complies with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products.

AJ. The use according to any one of example embodiments AB to AI, wherein the pharmaceutical composition further comprises at least one hydrophilic drug.

AK. An injectable pharmaceutical composition complying with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products comprising:
water,
one or more water soluble complexes, each comprising a cyclodextrin or a cyclodextrin derivative and a hydrophobic drug,
at least one preservative,
at least one co-solvent and
optionally a buffer effective to provide a pH in the composition in a range of from about 4.0 to about 9.0,
for treating an animal.

AL. The composition according to example embodiment AK, wherein the treating an animal is for at least one of the purposes of: anaesthetizing the animal, alleviating pain, or alleviating inflammation.

AM. An injectable pharmaceutical composition complying with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products comprising:
water,
one or more water soluble complexes, each comprising a cyclodextrin or a cyclodextrin derivative and a hydrophobic drug, at least one preservative,
at least one co-solvent and
optionally a buffer effective to provide a pH in the composition in a range of from about 4.0 to about 9.0, for treating a human being.

AN. The composition according to example embodiment AM, wherein the treating a human being is for the purpose of anaesthetizing the human being.

AO. A method of treating an animal, comprising administering to an animal an injectable pharmaceutical composition complying with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products, the composition comprising:
water,
one or more water soluble complexes, each comprising a cyclodextrin or a cyclodextrin derivative and a hydrophobic drug,
at least one preservative,
at least one co-solvent and
optionally a buffer effective to provide a pH in the composition in a range of from about 4.0 to about 9.0.

AP. The method according to example embodiment AO, wherein the method of treating an animal is for at least one of the purposes of: anaesthetizing the animal, alleviating pain, or alleviating inflammation.

AQ. A method of treating a human being, comprising the administering to a human being an injectable pharmaceutical composition complying with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products, the composition comprising:
water,
one or more water soluble complexes, each comprising a cyclodextrin or a cyclodextrin derivative and a hydrophobic drug,
at least one preservative,
at least one co-solvent and
optionally a buffer effective to provide a pH in the composition in a range of from about 4.0 to about 9.0.

AR. The method according to example embodiment AQ, wherein the method of treating a human being is for the purpose of anaesthetizing the human being.

AS. Use of an injectable pharmaceutical composition complying with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products comprising:
water,
one or more water soluble complexes, each comprising a cyclodextrin or a cyclodextrin derivative and a hydrophobic drug,
at least one preservative,
at least one co-solvent and
optionally a buffer effective to provide a pH in the composition in a range of from about 4.0 to about 9.0, in the preparation of a medicament for treating an animal.

AT. The use according to example embodiment AS, wherein the treating an animal is for at least one of the purposes of: anaesthetizing the animal, alleviating pain, or alleviating inflammation.

AU. Use of an injectable pharmaceutical composition complying with the European Pharmacopoeia 2011 Test for Efficacy of Antimicrobial Preservation, satisfying at least the B criteria for parenterals, and the United States Pharmacopeia 2011 Guidelines for Antimicrobial Effectiveness Testing for Category 1 (injectable) products comprising:
water,
one or more water soluble complexes, each comprising a cyclodextrin or a cyclodextrin derivative and a hydrophobic drug,
at least one preservative,
at least one co-solvent and
optionally a buffer effective to provide a pH in the composition in a range of from about 4.0 to about 9.0, in the preparation of a medicament for treating a human being.

AV. The use according to example embodiment AU, wherein the treating a human being is for the purpose of anaesthetizing the human being.

EXAMPLES

In order to better understand the nature of this invention, a number of illustrative examples will now be described. The scope of the invention is not limited to the examples provided below. The examples merely demonstrate the effectiveness of the invention.

Example 1: Compositions of the Invention Comprising Alfaxalone

Synthesis of Pharmaceutical Compositions Comprising Alfaxalone

Six different formulations: S, V, W, X, Y and Z, are shown in Table 1. All six formulations comprise alfaxalone but are composed of various solvents and preservatives in different amounts.

TABLE 1

Six examples of formulations, exemplifying the invention, which comprise alfaxalone as the hydrophobic drug.

| Component | Formulation S | Formulation V | Formulation W | Formulation X | Formulation Y | Formulation Z |
|---|---|---|---|---|---|---|
| Alfaxalone | 10 g | 10 g | 10 g | 10 g | 10 g | 10 g |
| 2-Hydroxypropyl-$\beta$-cyclodextrin | 80 g | 80 g | 80 g | 80 g | 80 g | 80 g |
| Sodium chloride (NaCl) | 8 g | 8 g | 8 g | 8 g | 8 g | 8 g |
| Disodium phosphate, anhydrous ($Na_2HPO_4$) | 940 mg | 940 mg | 940 mg | 940 mg | 940 mg | 940 mg |
| Potassium dihydrogen phosphate ($KH_2PO_4$) | 450 mg | 450 mg | 450 mg | 450 mg | 450 mg | 450 mg |

TABLE 1-continued

Six examples of formulations, exemplifying the invention, which comprise alfaxalone as the hydrophobic drug.

| Component | Formulation S | Formulation V | Formulation W | Formulation X | Formulation Y | Formulation Z |
|---|---|---|---|---|---|---|
| Glycerin | — | — | — | — | — | 100 g |
| Ethanol (undenatured) | 150 g | 150 g | 150 g | 100 g | 100 g | 100 g |
| Chlorocresol | 1.2 g | 1 g | 1.5 g | 1 g | 1 g | 1 g |
| Benzethonium chloride | — | 200 mg | 200 mg | — | 200 mg | 200 mg |
| Water for injection (WFI) | q.s. 1 L | q.s. 1 L | q.s. 1 L | q.s. 1 L | q.s. 1 L | q.s. 1 L |

The formulations of Table 1 were prepared according to the following standard procedure which is based on Formulation X:
1. 200 mL of WFI to was heated to 45° C.-50° C. Whilst mixing, 2-hydroxypropyl-β-cyclodextrin was slowly added. The solution was mixed until all the solid had completely dissolved.
2. Alfaxalone was added to the solution from Step 1. The solution was mixed until it turned clear.
3. The solution was made up to 400 mL using WFI.
4. Whilst stirring, NaCl, Na$_2$HPO$_4$, and KH$_2$PO$_4$ were added. The solution was mixed until all the salts had completely dissolved.
5. The pH of the solution was checked and adjusted to specification (6.0-7.5) using 10% HCl and 10% NaOH as required.
6. The ethanol was transferred to a separate container. Whilst stirring, chlorocresol was slowly added. It was mixed until all the solid had completely dissolved.
7. The solution from Step 6 was transferred to the bulk solution.
8. The solution was made up to volume (1 L) using WFI and mixed well.

When benzethonium chloride was incorporated into a formulation, it is added at Step 4 along with the buffering salts.

When glycerin was included in a formulation, it is added after the pH adjustment (Step 5) and prior to the addition of the chlorocresol in ethanol.

Stability Tests for Formulations X, Y and Z

Autoclaving the formulations for 20 minutes at 121° C. showed no significant decrease in alfaxalone concentration and the increase in degradation products was comparable to that in WO 01/70234 without preservative after autoclaving.

Storage of the formations at −20° C. and 0° C. for 3 months showed no detrimental effect on the active or preservative content. There was no apparent precipitation in the formulations.

Storage of the formulations for 12 months at 25° C./60% relative humidity (RH), 30° C./65% RH and 40° C./75% RH had no detrimental effect on the active or preservative content.

The inventors found that the addition of chlorocresol in the absence of a co-solvent caused the precipitation of the alfaxalone from a solution of water soluble complexes of alfaxalone and 2-hydroxypropyl-β-cyclodextrin. Similar effects were seen with benzyl alcohol, parabens, phenol, and phenylethanol. Titrations performed with benzyl alcohol showed significant precipitation occurring with a benzyl alcohol content of 0.2% w/v upwards to 1% w/v (typical content).

Preservation Studies for Formulations X, Y, Z, V and S

The formulations X, Y, and Z were examined against three microbes: *Pseudomonas aeruginosa* (*P. aeruginosa*) (bacteria, gram negative), *Escherichia coli* (*E. coli*) (bacteria, gram negative), and *Candida albicans* (*C. albicans*) (yeast). Formulations S and V were examined against five microbes: *Pseudomonas aeruginosa* (*P. aeruginosa*) (bacteria, Gram negative), *Escherichia coli* (*E. coli*) (bacteria, Gram negative), *Staphylococcus aureus* (*S. aureus*) (bacteria, Gram positive), *Candida albicans* (*C. albicans*) (yeast) and *Aspergillus brasiliensis* (*A. brasiliensis*) (mold). The European Pharmacopoeia 2011 Test for Efficacy of Antimicrobial Preservation, A and B criteria for parenterals, and the United States Pharmacopeia 2011 Guidelines for Antimicrobial Effectiveness Testing criteria for Category 1 (injectable) products are shown in Table 2. The antimicrobial tests for formulations X, Y, and Z in light of these criteria are shown in Table 3. The antimicrobial tests for formulations S and V in light of these criteria are shown in Table 4.

TABLE 2

The standards required for the injectable compositions in order to comply with the European Pharmacopoeia 2011 Test for Efficacy of Antimicrobial Preservation, A and B criteria for parenterals, and the United States Pharmacopeia 2011 Guidelines for Antimicrobial Effectiveness Testing criteria for Category 1 (injectable) products.

| | Log Reduction[a] | | | | |
|---|---|---|---|---|---|
| Guidelines | 6 hours | 24 hours | 7 days | 14 days | 28 days |
| Bacteria | | | | | |
| A Criteria | 2 | 3 | | | NR[b] |
| B Criteria | | 1 | 3 | | NI[c] |
| USP[d] | | | 1 | 3 | NI[c] |
| Fungi[f]/Yeast & Mold[f] | | | | | |
| A Criteria | | | 2 | | NI[c] |
| B Criteria | | | | 1 | NI[c] |
| USP[e] | | | NI[d] | NI[d] | NI[d] |

[a]Numerical values relate to the minimum log reduction required in relation to the initial readings/count;

[b]NR = no recovery;

[c]NI = no increase in number of viable micro-organisms compared to the previous reading;

[d]NI = no increase in the number of viable micro-organisms compared to the initial reading;

[e]category 1 criteria, applicable for injections;

[f]the term "Fungi" is used in the European Pharmacopoeia 2011 Test for Efficacy of Antimicrobial Preservation; the phrase "Yeast & Mold" is applied to the United States Pharmacopeia 2011 Guidelines for Antimicrobial Effectiveness Testing.

TABLE 3

Assessing the antimicrobial effects for Formulations X, Y, and Z on
P. aeruginosa, E. coli and C. albicans. Where the test complies with the A criteria for
parenterals according to the European Pharmacopoeia 2011 Test for Efficacy of
Antimicrobial Preservation and the Category 1 (injectable) criteria according to the
United States Pharmacopeia 2011 Guidelines for Antimicrobial Effectiveness Testing,
"(Pass)" is shown.

| Formulation | Preservative(s) | Co-solvent(s) | Challenge Microbe | Acceptance Criteria Results [Log] Reduction From Inoculation | |
|---|---|---|---|---|---|
| | | | | 24 hours | 7 days |
| X | 0.1% Chlorocresol | 10% Ethanol | P. aeruginosa | 6.0 (Pass) | N/A |
| | | | E. coli | 6.1 (Pass) | N/A |
| | | | C. albicans | N/A | 4.2 (Pass) |
| Y | 0.1% Chlorocresol + 0.02% Benzethonium chloride | 10% Ethanol | P. aeruginosa | 6.0 (Pass) | N/A |
| | | | E. coli | 6.1 (Pass) | N/A |
| | | | C. albicans | N/A | 5.2 (Pass) |
| Z | 0.1% Chlorocresol + 0.02% Benzethonium chloride | 10% Glycerin + 10% Ethanol | P. aeruginosa | 6.0 (Pass) | N/A |

The results from Table 3 show that the formulations X, Y, and Z comply with the European Pharmacopoeia 2011 Test for Efficacy of Antimicrobial Preservation, A criteria for parenterals, and the United States Pharmacopeia 2011 Guidelines for Antimicrobial Effectiveness Testing criteria for Category 1 (injectable) products and incidentally, the European Pharmacopoeia 2011 Test for Efficacy of Antimicrobial Preservation B criteria for parenteral products. Compliance for Formulations X, Y, and Z was only assessed for 3 of 5 microbes at 24 hour (P. aeruginosa and E. coli) and 7 days (C. albicans) unlike Formulation S and V which were assessed using all the necessary microbes from 6 hour post inoculation to 28 days for a 28 day shelf-life after initial broaching of the product.

TABLE 4

Assessing the antimicrobial effects for Formulations S and V on
P. aeruginosa, E. coli S. aureus, C. albicans and A. brasiliensis. Where the test
complies with the A criteria for parenterals according to the European Pharmacopoeia
2011 Test for Efficacy of Antimicrobial Preservation and the Category 1 (injectable)
criteria according to the United States Pharmacopeia 2011 Guidelines for Antimicrobial
Effectiveness Testing, "(Pass)" is shown.

| Formulation | Preservative(s) | Co-solvent | Challenge Microbe | Acceptance Criteria Results [Log] Reduction From Inoculation | | | | |
|---|---|---|---|---|---|---|---|---|
| | | | | 6 hours | 24 hours | 7 days | 14 days | 28 days |
| S | 0.12% Chlorocresol | 15% Ethanol | P. aeruginosa | 5.3 (Pass) | 5.3 (Pass) | N/A | N/A | 5.3 (*Pass) |
| | | | E. coli | 5.2 (Pass) | 5.2 (Pass) | N/A | N/A | 5.2 (*Pass) |
| | | | S. aureus | 3.2 (Pass) | 5.8 (Pass) | 5.8 (Pass) | N/A | 5.8 (*Pass) |
| | | | C. albicans | N/A | N/A | 5.8 (Pass) | 5.8 (Pass) | 5.8 (†Pass) |
| | | | A. brasiliensis | N/A | N/A | 3.4 (Pass) | 5.1 (Pass) | 5.1 (†Pass) |
| V | 0.1% Chlorocresol + 0.02% Benzethonium chloride | 15% Ethanol | P. aeruginosa | 5.9 (Pass) | 5.9 (Pass) | N/A | N/A | 5.9 (*Pass) |
| | | | E. coli | 5.8 (Pass) | 5.8 (Pass) | N/A | N/A | 5.8 (*Pass) |
| | | | S. aureus | 3.0 (Pass) | 6.0 (Pass) | 6.0 (Pass) | N/A | 6.0 (*Pass) |
| | | | C. albicans | N/A | N/A | 5.8 (Pass) | 5.8 (Pass) | 5.8 (†Pass) |
| | | | A. brasiliensis | N/A | N/A | 3.9 (Pass) | 4.7 (Pass) | 4.7 (†Pass) |

*No recovery (NR) of microorganisms at 28 days post-inoculation (EP-A).
†No increase (NI) in microbial concentration from 7 to 28 days post-inoculation (EP-A).

The results from Table 4 Preservative efficacy testing of Formulations S and V show that both formulations meet the requirements of the European Pharmacopoeia 2011 Test for Efficacy of Antimicrobial Preservation A criteria for a parenteral or ophthalmic product against the microorganisms: *Pseudomonas aeruginosa, Escherichia coli, Staphylococcus aureus, Candida albicans* and *Aspergillus brasiliensis* at 6 and 24 hours, and 7, 14 and 28 days post-inoculation. Hence, Formulations S and V also satisfy the United States Pharmacopeia 2011 Guidelines for Antimicrobial Effectiveness Testing criteria for Category 1 (injectable) products and the European Pharmacopoeia 2011 Test for Efficacy of Antimicrobial Preservation B criteria for parenterals.

Example 2: Compositions of the Invention Comprising Meloxicam

Synthesis of Pharmaceutical Compositions Comprising Meloxicam

TABLE 5

An exemplified composition of the invention comprising meloxicam, Formulation U.

| Component | Amount (g/L) |
|---|---|
| Meloxicam | 5.0 |
| 2-Hydroxypropyl-β-cyclodextrin | 21.0 |
| Plasdone ® K25 | 5.0 |
| Ethanol | 150.0 |
| Chlorocresol | 1.0 |
| Sodium Chloride | 9.0 |
| Water For Injection (WFI) | q.s. 1 L |

Formulation U was prepared according to the following procedure:
1. 600 mL of WFI to was transferred to a beaker. Whilst stirring, sodium chloride was added and the solution mixed until all solid was completely dissolved.
2. Whilst mixing, 2-hydroxypropyl-β-cyclodextrin and Plasdone® K25 (obtainable from International Specialty Products Inc. (ISP)) was slowly added. Plasdone® K25 is a pharmaceutical grade poly(l-vinyl-2-pyrrolidone) with a molecular weight of approximately 34000. The solution was mixed until all the solid had completely dissolved.
3. Meloxicam was added to the solution from Step 1. The solution was mixed until all solid was completely suspended.
4. The pH of the solution was adjusted to 12.0-12.5 using sodium hydroxide solutions as required. The solution was stirred until clear.
5. The pH of the clear solution was adjusted to 8-9 using hydrochloric acid solution.
6. The ethanol was transferred to a separate container. Whilst stirring, chlorocresol was slowly added. It was mixed until all the solid had completely dissolved.
7. The solution from Step 6 was transferred to the bulk solution.
8. The solution was made up to volume (1 L) using WFI and mixed well.

Stability Tests

Formulation U shows no significant change to active or preservative content when stored for 6 months at 30° C./65% RH.

Preservation Studies

Preservative efficacy testing of Formulation U showed it to meet the requirements for USP 2011 for efficacy of Anti-Microbial Preservation for a parenteral or ophthalmic product against the microorganisms *Pseudomonas aeruginosa, Escherichia coli, Staphylococcus aureus, Candida albicans* and *Aspergillus brasiliensis* 7, 14 and 28 days post-inoculation

TABLE 6

Preservative Efficacy Test - United State Pharmacopeia 2011 Parenteral & Ophthalmic - Formulation U.[a]

| Time point | S. aureus AMS 027 (ATCC 6538) | P. aeruginosa AMS 095 (ATCC 9027) | E. coli AMS 006 (ATCC 8739) | C. albicans AMS 003 (ATCC 10231) | A. niger AMS 032 (ATCC 16404) |
|---|---|---|---|---|---|
| Inoculum cfu/ml | $9.1 \times 10^5$ | $4.0 \times 10^5$ | $7.4 \times 10^5$ | $8.9 \times 10^5$ | $1.6 \times 10^5$ |
| 0 days | $8.5 \times 10^5$ | $2.8 \times 10^5$ | $6.4 \times 10^5$ | $6.7 \times 10^5$ | $1.7 \times 10^5$ |
| 7 days | <10 | <10 | <10 | <10 | <10 |
| 14 days | <10 | <10 | <10 | <10 | <10 |
| 28 days | <10 | <10 | <10 | <10 | <10 |

[a]All results are expressed as cfu (colony forming unit) per ml.

Example 3: Compositions of the Invention Comprising Carprofen

Synthesis of Pharmaceutical Compositions Comprising Carprofen

Table 7 lists the components required to make 1 L of Formulation T.

TABLE 7

An exemplified composition of the invention comprising carprofen, Formulation T.

| Component | Formulation T |
|---|---|
| Carprofen | 50 g |
| 2-Hydroxypropyl-β-cyclodextrin | 200 g |
| Sodium hydroxide (NaOH) | 12 g |
| Hydrochloric acid (10M) | 11 g |
| Ethanol (undenatured) | 100 g |
| Chlorocresol | 1 g |
| Water for injection (WFI) | q.s. 1 L |

Formulation T was prepared according to the following:
1. 400 mL of WFI to was transferred to a beaker. Whilst stirring, 2-Hydroxypropyl-β-cyclodextrin was added slowly and the solution heated to 50° C. until all solid was completely dissolved.
2. Sodium hydroxide was added to the solution. The solution was mixed until all solid was completely dissolved.
3. Carprofen was added to the solution from Step 2. The solution was mixed until all solid was completely dissolved.
4. The pH of the solution was adjusted to 7.5-8.0 using hydrochloric acid solution.
5. The ethanol was transferred to a separate container. Whilst stirring, chlorocresol was slowly added. It was mixed until all the solid had completely dissolved.
6. The solution from Step 5 was transferred to the bulk solution after it was cooled to room temperature.
7. The solution was made up to volume (1 L) using WFI and mixed well.

Stability Tests for Formulation T

Formulation T shows no significant change to the active or preservative content when stored for 6 months at 40° C./75% RH.

Preservation Studies for Formulation T

Preservative efficacy testing of Formulation T showed it to meet the European Pharmacopoeia 2011 Test for Efficacy of Antimicrobial Preservation A criteria and the United States Pharmacopeia 2011 Guideline requirements for efficacy of Anti-Microbial Preservation against the five reference microorganisms (*P. aeruginosa, E. coli, S. aureus, C. albicans* and *A. brasiliensis*) at the sampling time points 0, 6 and 24 hours, 7 and 14 days for a parenteral or ophthalmic product.

Example 4: Animal Studies

Efficacy and Safety of Formulation Y in Mice:

JX9604.08-K012 "A study in mice investigating the comparative anaesthetic efficacy and safety of Jurox formulations RD0304 and Alfaxan® at a clinical dose rate". The animal phase of this study was completed 21 Feb. 2012. Study personnel were blinded to treatment groups.

The study demonstrated the following:
1. Treatment of mice with Alfaxan® and Formulation Y (RD0304) did not result in any morbidity or mortality.
2. The anesthetic efficacy of the test article Formulation Y was comparable to that of the reference article Alfaxan® in the test conditions of this study.
3. The two formulations were well-tolerated and resulted in a comparable duration and quality of anesthesia.

Alfaxan® is an intravenous injectable anesthetic comprising complexes of alfaxalone and 2-hydroxy-β-cyclodextrin (obtainable from Jurox Pty Ltd).

Safety and Efficacy of Formulation W in Dogs

JX9604.08-K013 "The comparative safety and efficacy of Alfaxan® plus preservatives versus Alfaxan® at a dose rate of 2 mg alfaxalone/kg body weight as an intravenous anesthetic induction agent in dogs". The animal phase of this study was completed 10 May 2012. Study personnel were blinded to treatment groups.

This was a two-period, cross-over study involving twelve mixed breed dogs. Outcome measures consisted of alfaxalone concentration over time measurements during clearance, quality and duration of anesthesia, and physiological variables such as pulse rate, respiratory rate, oxygen saturation of hemoglobin concentration, end-tidal $CO_2$ and non-invasive blood pressure.

The study results demonstrated the following:
1. Treatment of dogs with Alfaxan® and Formulation W (RD0307) did not result in any morbidity or mortality.
2. Secondary pharmacokinetics generated from plasma alfaxalone concentration over time data (FIG. 1) showed that the two pivotal parameters for bioequivalence (i.e. area under the curve [AUC] and maximum blood concentration [$C_{max}$]) were similar.
3. Quality of anesthesia was similar between Alfaxan® and Formulation W.
4. Physiological variables measured during anesthesia remained within clinically acceptable limits with both Alfaxan® and Formulation W. Anesthetic induction, anesthesia and recovery times were also comparable between both formulations.

FIG. 1 discloses the concentration of alfaxalone in plasma (mg/L) versus time after IV administration of Alfaxan® or Formulation W to dogs (n=12 per time point).

Safety and Efficacy of Formulation W in Cats:

JX9604.08-K014 "The comparative safety and efficacy of Alfaxan® plus preservatives versus Alfaxari at a dose rate of 5 mg alfaxalone/kg body weight as an intravenous anesthetic induction agent in cats". The animal phase of this study was completed 27 Jun. 2012. Study personnel were blinded to treatment groups.

This was a two-period, cross-over study involving twelve domestic short-haired cats. Outcome measures consisted of alfaxalone concentration over time measurements during clearance, quality and duration of anesthesia, and physiological variables such as pulse rate, respiratory rate, oxygen saturation of hemoglobin concentration, end-tidal $CO_2$ and non-invasive blood pressure.

Figure 2:
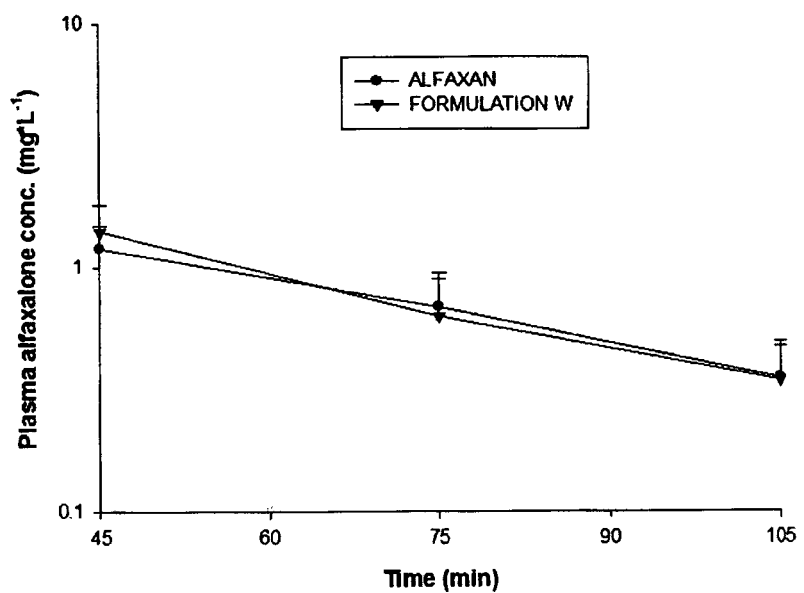
FIG. 2—Discloses the concentration of alfaxalone in plasma (mg/L) versus time after IV administration of Alfaxan® or Formulation W (Table 1) to cats (n=12 per time point).

The study results demonstrated the following:
1. Treatment of cats with Alfaxan® and Formulation W (RD0307) did not result in any morbidity or mortality.
2. Secondary pharmacokinetics generated from plasma alfaxalone concentration over time data (FIG. 2) showed that the two pivotal parameters for bioequivalence (i.e. area under the curve [AUC] and maximum blood concentration [$C_{max}$]) were similar.
3. Quality of anesthesia was similar between Alfaxan® and Formulation W.
4. Physiological variables measured during anesthesia remained within clinically acceptable limits with both Alfaxan® and Formulation W. Anesthetic induction, anesthesia and recovery times were also comparable between both formulations. FIG. 2 discloses the concentration of alfaxalone in plasma (mg/L) versus time after IV administration of Alfaxan® or Formulation W to cats (n=12 per time point).

It will be appreciated by persons skilled in the art that numerous variations and/or modifications may be made to the invention as shown in the specific embodiments without departing from the scope of the invention as broadly described. The present embodiments are, therefore, to be considered in all respects as illustrative and not restrictive.

What is claimed is:

1. A method of anaesthetizing one or more subjects using a composition stored in a sealed multi-dose container, the composition comprising:
   water,
   one or more water soluble complexes, each comprising a β-cyclodextrin and a hydrophobic drug selected from the group consisting of alfaxalone, propofol, meloxicam and carprofen;
   at least one preservative selected from the group consisting of: m-cresol, chlorocresol, methylparaben, ethylparaben, propylparaben, butylparaben, chlorobutanol, benzethonium chloride, benzalkonium chloride, boric acid, benzyl alcohol, cetylpyridinium chloride, cetrimide, phenol, phenylethanol and phenoxyethanol;
   at least one co-solvent comprising 10% w/v to 15% w/v ethanol; and
   optionally a buffer effective to provide a pH in the composition in a range of from about 4.0 to about 9.0, the method comprising:
   broaching the sealed multi-dose container and withdrawing a first anaesthetically effective dose of said composition and administering the dose to a first of said subjects; and subsequently withdrawing further anaesthetically effective doses, if required, and administering the doses to further subjects either until no further doses are available in the container or at least 28 days have elapsed since the first dose was withdrawn, wherein the injectable pharmaceutical composition complies with the European Pharmacopoeia 2011 Test for Efficacy of Antimicrobial Preservation, satisfying at least the B criteria for parenterals and the United States Pharmacopeia 2011 Guidelines for Antimicrobial Effectiveness Testing for Category 1 (injectable) products following the withdrawal of the first anaesthetically effective dose.

2. The method according to claim 1, wherein the hydrophobic drug is alfaxalone.

3. The method according to claim 1, wherein the injectable pharmaceutical composition comprises 1% w/v to 5% w/v alfaxalone.

4. The method according to claim 1, wherein the β-cyclodextrin is 2-hydroxypropyl-β-cyclodextrin or a sulfoalkyl ether β-cyclodextrin.

5. The method according to claim 1, wherein the cyclodextrin or cyclodextrin derivative is 2-hydroxypropyl-β-cyclodextrin.

6. The method according to claim 1, wherein the buffer effective to stabilise the hydrophobic drug and provide a pH in the composition in a range of from about 4.0 to about 9.0 is selected from the group consisting of: phosphate based buffers, acid-phosphate based buffers, citrate based buffers, and combinations thereof.

7. A method of anaesthetizing one or more subjects using a composition stored in a sealed multi-dose container comprising: per liter of water,
   80 g 2-hydroxypropyl-β-cyclodextrin;
   10 g alfaxalone;
   8 g sodium chloride;
   940 mg disodium phosphate;
   450 mg potassium dihydrogen phosphate;
   100 to 150 g ethanol; and
   1 g to 1.5 g chlorocresol,
   wherein the pH is adjusted to a pH in a range of 6.0 to 7.5 using a pH adjuster, the method comprising:
   broaching the sealed multi-dose container and withdrawing a first anaesthetically effective dose of said composition and administering the dose to a first of said subjects;
   and subsequently withdrawing further anaesthetically effective doses, if required, and administering the doses to further subjects either until no further doses are available in the container or at least 28 days have elapsed since the first dose was withdrawn, wherein the injectable pharmaceutical composition complies with the European Pharmacopoeia 2011 Test for Efficacy of Antimicrobial Preservation, satisfying at least the B criteria for parenterals and the United States Pharmacopeia 2011 Guidelines for Antimicrobial Effectiveness Testing for Category 1 (injectable) products following the withdrawal of the first anaesthetically effective dose.

8. The method according to claim 7, wherein the injectable pharmaceutical composition further comprises 200 mg benzethonium chloride.

9. A method of anaesthetizing one or more subjects using a composition stored in a sealed multi-dose container and comprising:
   1% w/v to 5% w/v alfaxalone;
   8% w/v to 40% w/v 2-hydroxypropyl-β-cyclodextrin;
   0.1% w/v to 0.15% w/v chlorocresol;
   15% w/v ethanol; and
   optionally a phosphate based buffer to provide a pH in a range of 6.0 to 7.5, comprising:
   broaching the sealed multi-dose container and withdrawing a first anaesthetically effective dose of said composition and administering the dose to a first of said subjects;
   and subsequently withdrawing further anaesthetically effective doses, if required, and administering the doses to further subjects either until no further doses are available in the container or at least 28 days have elapsed since the first dose was withdrawn, wherein the injectable pharmaceutical composition complies with the European Pharmacopoeia 2011 Test for Efficacy of Antimicrobial Preservation, satisfying at least the B criteria for parenterals and the United States Pharmacopeia 2011 Guidelines for Antimicrobial Effectiveness Testing for Category 1 (injectable) products following the withdrawal of the first anaesthetically effective dose.

10. The method of claim 9, wherein the phosphate based buffer comprises disodium phosphate and potassium dihydrogen phosphate.

11. The method according to claim 9, wherein the injectable pharmaceutical composition further comprises from 0.005% w/v to 0.05% w/v of benzethonium chloride.

12. The method according to claim 9, wherein the injectable pharmaceutical composition further comprises 0.01% w/v to 0.02% w/v of benzethonium chloride.

* * * * *